United States Patent [19]

Klimesch et al.

[11] Patent Number: 4,880,585
[45] Date of Patent: Nov. 14, 1989

[54] CONTINUOUS METHOD OF TABLETING

[75] Inventors: Roger G. Klimesch, Alsbach/Haehnlein; Gerhard Bleckmann, Lampertheim; Karl-Peter Farwerck, Worms; Hans-Helmut Goertz, Freinsheim; Lothar Schlemmer, Maxdorf, all of Fed. Rep. of Germany

[73] Assignee: BASF Aktiengesellschaft, Ludwigshafen, Fed. Rep. of Germany

[21] Appl. No.: 289,407

[22] Filed: Dec. 22, 1988

Related U.S. Application Data

[63] Continuation of Ser. No. 34,939, Apr. 6, 1987, abandoned, which is a continuation-in-part of Ser. No. 923,870, Oct. 28, 1986, abandoned.

[30] Foreign Application Priority Data

Apr. 11, 1986 [DE] Fed. Rep. of Germany ....... 3612211

[51] Int. Cl.$^4$ .......................... A61K 9/20; B29C 43/02; B29C 47/00
[52] U.S. Cl. .................... 264/141; 264/151; 264/163; 264/167; 264/210.2; 264/297.5; 264/325; 264/331.19; 425/112; 425/115; 425/116; 425/121; 425/122; 425/327; 425/363; 424/486
[58] Field of Search ............ 264/141, 151, 167, 210.2, 264/211.12, 280, 282, 297.5, 320, 325, 331 A; 425/112, 115, 116, 121, 122, 327, 363, 408; 424/486

[56] References Cited

U.S. PATENT DOCUMENTS

| | | | |
|---|---|---|---|
| 99,083 | 1/1870 | Hart | 425/116 X |
| 2,988,774 | 6/1961 | Hely | 264/151 |
| 3,755,527 | 8/1973 | Keller et al. | 264/141 X |
| 3,758,679 | 9/1973 | Seidler | 264/141 X |
| 3,843,299 | 10/1974 | Bochanov et al. | 425/363 X |
| 3,859,407 | 1/1975 | Blanding et al. | 425/116 X |
| 3,936,522 | 2/1976 | Franz | 264/141 |
| 4,028,024 | 6/1977 | Moreland | 425/327 X |
| 4,130,521 | 12/1978 | Katsumoto | 264/142 X |
| 4,191,723 | 3/1980 | Vargiu et al. | 264/151 X |
| 4,256,448 | 3/1981 | Carle | 425/192 R X |
| 4,340,557 | 7/1982 | Gross | 264/163 X |
| 4,411,611 | 10/1983 | Ohtawa et al. | 425/237 |
| 4,451,260 | 5/1984 | Mitra | 604/890 |
| 4,520,179 | 5/1985 | Barabas et al. | 526/212 |
| 4,520,180 | 5/1985 | Barabas et al. | 526/212 |
| 4,569,837 | 2/1986 | Suzuki et al. | 514/781 |
| 4,801,460 | 1/1989 | Goertz et al. | 424/465 |

FOREIGN PATENT DOCUMENTS 1766546 9/1971 Fed. Rep. of Germany .
537444 5/1922 France .

Primary Examiner—Jeffery Thurlow
Assistant Examiner—Leo B. Tentoni
Attorney, Agent, or Firm—Keil & Weinkauf

[57] ABSTRACT

Extrudable pharmaceutical mixtures are tableted by a continuous method in which the mixture is extruded and the still deformable extrudate is pressed between two rollers which are driven in opposite directions and possess depressions opposite one another in the roller shell, the form of these depressions determining the tablet shape.

3 Claims, 1 Drawing Sheet

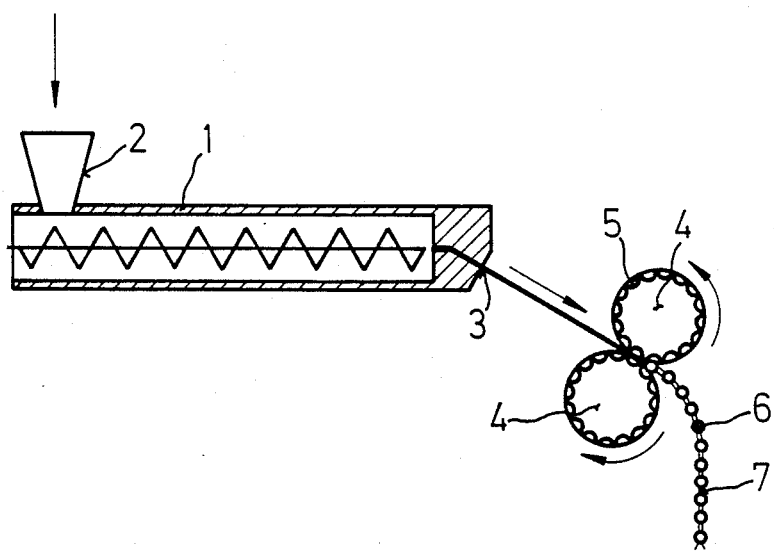

CONTINUOUS METHOD OF TABLETING

This application is a continuation application Ser. No. 034,939 filed Apr. 6, 1987, now abandoned, which is a continuation-in-part of application Ser. No. 923,870, filed Oct. 28, 1986, now abandoned.

BACKGROUND AND OBJECTS OF THE INVENTION

The present invention relates to a simple, continuous method for the preparation of tablets.

The conventional tableting presses operate on the basis of a cycle, using punches and dies. The process requires thoroughly premixed tableting materials and overall is therefore an expensive multistage process.

It is an object of the present invention to provide a simple, continuous method of tableting. We have found that this object is achieved by a continuous method for tableting extrudable pharmaceutical mixtures, wherein the mixture is extruded and the still deformable extrudate is pressed between two rollers which are driven in opposite directions and possess depressions opposite one another in the roller shell, the form of these depressions determining the tablet shape. If hemispherical tablets or other tablets which are flat on one side are to be prepared, one roller shell is left smooth.

Although there may be cases in which premixing is advantageous, so that a simple extruder is adequate, it is as a rule substantially more advantageous if the extruder, in the conventional manner, is in the form of a single-screw or multi-screw mixing extruder, thus making premixing unnecessary.

DESCRIPTION OF THE DRAWING

The drawing is a schematic, cross-sectional view of apparatus that can be used in carrying out the invention.

DETAILED DESCRIPTION OF THE INVENTION

The mixing extruder (1) may possess a plurality of feed orifices (2), if necessary for feeding solid and liquid components of the mixture separately, and a pipe connection for introduction of an inert gas (as a rule nitrogen) and/or devolatilization. In order to increase the throughput, the extruder may have more than one die (3).

To ensure reliable transportation of the extrudate and to prevent it from breaking off downstream of the die, it is advantageous to carry out extrusion obliquely in a downward direction. The most advantageous angle in each case depends on the product properties and the procedure (eg. extrusion temperature and extrusion velocity).

The shaping procedure is carried out directly after the extrusion process. The still plastic extrudate is fed through a pair of rollers (4), if necessary with the aid of a suitable guide channel, the shells of the two rollers possessing depressions (5) which are located opposite one another and, in pairs, generate the tablet shape at the line of contact.

In a preferred embodiment, particularly for tacky materials which adhere to a greater or lesser extent to the mold wall (depressions 5), the depressions are connected to one another by an open channel, so that the shaped tablets (6) remain connected to one another via a short web (nominal breaking point, 7). Depending on the flexibility of the material, this procedure gives structures which are rigid or in the form of a string of pearls and contain a plurality of tablets.

The structures resembling a string of pearls can be rolled up, and packaged in an economical manner with the aid of relatively simple machines. The rigid structures can be broken up to give a desired length or into individual tablets.

If the adhesion of the resulting tablets to the mold walls (the depressions in the roller shells) is sufficiently low that even individual tablets (not connected via webs) do not remain adhering but fall freely out of the depressions, the stated connecting webs can be dispensed with. In this case, elongated depressions (for oblong tablets or suppositories) are advantageously arranged parallel to the longitudinal axis of the roller.

In general, natural air cooling is sufficient for the rollers. In special cases, it may be advantageous to cool them additionally or to heat them. For such cases, the rollers should advantageously be heatable, ie. possess one of the conventional constructions for passing through a liquid cooling or heating medium.

If the extruder has more than one die, each die is of course associated with a number of shape-imparting depressions (5) which run around each roller circumference in a plane at right angles to the axis.

The novel method is the first continuous method for tableting pharmaceutical mixtures. It is not only simpler, more effective and hence more economical than the conventional preparation by means of the conventional tableting presses but also has other important advantages:

1. more latitude in designing the tablet shape (eg. spherical)

2. tacky and/or highly viscous material which can be processed on a conventional tableting press only with great difficulty, if at all, can be processed because the weight of the connected tablets is capable of overcoming the adhesive force between the tablet and the mold half.

Extrudable pharmaceutical mixtures are mixtures of one or more pharmaceutical active compounds with one or more auxiliaries conventionally used for the preparation of pharmaceutical tablets; by conversion to a paste with, for example, water at elevated temperatures (not less than 70° C.) or by melting or softening of one or more components, the said mixtures become extrudable. The mixtures in question are, in particular, those which contain pharmacologically acceptable polymers (the glass transition temperature of the mixture being below the decomposition temperature of all components of the mixture), eg. polyvinylpyrrolidone (PVP), copolymers of N-vinylpyrrolid-2-one (NVP) and vinyl acetate, copolymers of vinyl acetate and crotonic acid, partially hydrolyzed polyvinyl acetate, polyvinyl alcohol, ethylene/vinyl acetate copolymers, polyhydroxyethyl methacrylate, copolymers of methyl methacrylate and acrylic acid, cellulose esters, cellulose ethers, polyethylene glycol or polyethylene. The K values (according to H. Fikentscher, Cellulose-Chemie 13 (1932), 58–64 and 71 and 74) of the polymers are from 10 to 100, preferably from 12 to 70, in particular from 12 to 35, and for PVP preferably from 12 to 35, in particular from 12 to 17.

In the total mixture of all components, the polymeric binder should soften or melt at from 50° to 180° C., preferably from 60° to 130° C., so that the material is extrudable. The glass transition temperature of the mixture must in any case therefore be less than 180° C., preferably less than 130° C. If necessary, it is reduced by means of conventional pharmacologically acceptable plasticizers, such as long-chain alcohols, ethylene glycol, propylene glycol, trimethylolpropane, triethylene glycol, butanediols, pentanols, hexanols, polyethylene glycols, silicones, aromatic carboxylates (eg. dialkyl phthalates, trimellitates, benzoates or terephthalates), aliphatic dicarboxylates (eg. dialkyl adipates, sebacates, azelates, citrates and tartrates) or fatty acid esters.

NPV polymers which, in the mixture with the active compound and, where appropriate, conventional pharmaceutical auxiliaries, with or preferably without added plasticizers, melt or soften in the desired temperature range are preferred. Melting or softening below a certain temperature may be necessary in view of possible thermal and/or oxidative damage not only to the active compound but also to the NVP polymer. This may cause yellowing during extrusion, which is the reason why NVP polymers have not usually been extruded to date. However, there is little danger at extrusion temperatures below 180° C., especially below 130° C., if the polymer has been prepared not in aqueous solution using hydrogen peroxide as an initiator, but in an organic solvent, or in water using an organic peroxide as an initiator, for example by the process according to German Patent Application P No. 36 42 633.4 or that described in U.S. Pat. Nos. 4,520,179 and 4,520,180.

If the K value is greater than 17, in particular greater than 30 or even 40 (up to a maximum of 70), and no strong plasticizer has been added, the only suitable NVP polymers are those having a glass transition temperature Tg of less than 120° C., preferably less than 100° C., or the NVP polymer (including homopolymers) must not have been prepared in water using $H_2O_2$ as an initiator. This would in fact give rise to terminal groups in the polymer which lead to yellowing at elevated temperatures.

Depending on the intended use, the NVP polymer can be rendered, via the type and amount of comonomers, sufficiently strongly or weakly hydrophilic that the tablets prepared from the said polymer dissolve in the mouth (buccal tablets), in the stomach or not until they reach the intestine (rapidly or gradually) or swell so that they realease the active compound. They are sufficiently swellable when they absorb more than 10% by weight of water when stored at 90% relative humidity. If it is desirable for carboxyl-containing binders to release the active compound only in the alkaline medium of the intestine, the above water absorption applies only to the neutralized form (salt form) of the polymer (in which some or all of the protons of the carboxyl groups are replaced with ammonium, sodium or potassium ions).

Suitable comonomers for NVP are unsaturated carboxylic acids, eg. methacrylic acid, crotonic acid, maleic acid or itaconic acid, their esters with alcohols of 1 to 12, preferably 1 to 8, carbon atoms, hydroxyethyl and hydroxypropyl acrylate and methacrylate, (meth)acrylamide, the anhydrides and half esters of maleic acid and itaconic acid (the half esters preferably not being formed until polymerization is complete), N-vinylcaprolactam and vinyl propionate. Preferred comonomers are acrylic acid and in particular vinyl acetate. NVP homopolymers or NVP polymers which contain vinyl acetate as the sole comonomer are therefore preferred. Vinyl acetate and vinyl propionate may be completely or partly hydrolyzed after the polymerization.

Conventional pharmaceutical auxiliaries, which may be present in a total amount of up to 100% by weight, based on the polymer, are, for example, extenders, such as silicates or siliceous earth, stearic acid or its salts with, for example, magnesium or calcium, methylcellulose, sodium carboxymethylcellulose, talc, sucrose, lactose, cereal starch or corn starch, potato flour or polyvinyl alcohol, wetting agents, preservatives, disintegrating agents, adsorbents, dyes and flavorings (cf. for example H. Sucker et al., Pharmazeutische Technologie, Thieme Verlag, Stuttgart 1978).

If desired, the tablet prepared according to the invention may also be provided with conventional coating to improve the appearance and/or the taste (coated tablet) or additionally to delay the release of active compound. In the case of oral tablets with sustained release of the active compound, it may be advantageous to produce the tablet, by a conventional technique, in a closed-cell porous form, so that it floats in the stomach and thus remains there longer. The novel process can also be used to produce very small tablets, which are advantageously introduced into capsules in place of conventional granules. For the purposes of the present invention, the term tablet is not restricted to a certain shape or to peroral administration. Instead, it also includes suppositories for rectal administration (which do not melt at body temperature).

For the purposes of the present invention, pharmaceutical active compounds are all substances which have a pharmaceutical effect and a very low level of side effects, provided that they do not decompose under the processing conditions. The amount of active compound per dosage unit and the concentration can vary within wide limits, depending on the activity and rate of release. The only condition is that they are sufficient to achieve the desired effect. For example, the concentration of active compound can be from 0.1 to 95, preferably from 20 to 80, in particular from 30 to 70, % by weight. Combinations of active compounds may also be used. For the purposes of the present invention, active compounds include vitamins.

In the Examples which follow, parts and percentages are by weight.

EXAMPLE 1

45 parts of a copolymer obtained from 60% by weight of N-vinylpyrrolidone and 40% by weight of vinyl acetate and having a K value of 30, 5 parts of stearyl alcohol and 50 parts of theophyllin were mixed in a twin-screw extruder and extruded. The temperatures of the six shots at the extruder barrel were 30°, 60°, 60°, 60°, 60° and 60° C.; the die was heated to 100° C. The extrudate obtained was pressed directly to oblong tablets, using the apparatus described above. The resulting rigid tablet strands broke up very readily into the individual tablets. The tablets thus obtained were stable to mechanical influences and showed no abrasion during transportation and packaging.

EXAMPLE 2

50 parts of the copolymer of Example 1 and 50 parts of theophyllin were mixed in a twin-screw extruder and extruded. In contrast to Example 1, the temperatures of the shots were brought to 30°, 60°, 60°, 60°, 90° and 120° C. The die was likewise at 120° C. The extrudate obtained was pressed to give oblong tablets similarly to Example 1, using the apparatus described above. These tablets were also stable to mechanical influences.

EXAMPLE 3

47.5 parts of a copolymer obtained from 60% by weight of N-vinylpyrrolidone and 40% by weight of vinyl acetate and having a K value of 30, 2.5 parts of crosslinked PVP, as a tablet disintegrator, and 50 parts of theophyllin were mixed in a twin-screw extruder and extruded. The five shots were each at 120° C., and the die was at 130° C. The still plastic extrudate was pressed to give oblong tablets, as described in Example 1. The tablets were stable to mechanical influences.

EXAMPLE 4

50 parts of a copolymer obtained from 30% by weight of N-vinylpyrrolidone and 70% by weight of vinyl acetate and having a K value of 52 and 50 parts of theophyllin were mixed in a twin-screw extruder and extruded. The five shots were at 30°, 60°, 100°, 100° and 120° C. The die was likewise heated to 120° C. The still plastic extrudate was pressed to give mechanically stable oblong tablets, as described in Example 1.

EXAMPLES 5 TO 8

A mixture of 50% by weight of N-vinylpyrrolidone homopolymer (PVP) having the K value stated in each case in the Table and 50% by weight of theophyllin was melted in a single-screw extruder at the particular temperature stated in the Table, extruded, and shaped into tablets as described in Example 1.

| Example | K value | 1 | 2 | 3 Shot | 4 | 5 | Die |
|---|---|---|---|---|---|---|---|
| 5 | 12 | 115 | 125 | 135 | 135 | 135 | 145 |
| 6 | 17 | 125 | 125 | 135 | 145 | 145 | 155 |
| 7 | 25 | 145 | 155 | 165 | 175 | 175 | 175 |
| 8 | 30 | 150 | 160 | 160 | 170 | 180 | 180 |
| 8a | 60 | 150 | 160 | 160 | 170 | 180 | 180 |

T [°C.]

EXAMPLE 9

40 parts of a copolymer obtained from 60% by weight of N-vinylpyrrolidone and 40% by weight of vinyl acetate and having a K value of 30, 10 parts of polyhydroxyethyl methacrylate and 50 parts of theophyllin were processed to mechanically stable tablets by a method similar to that described in Example 1. The temperatures of the shots were 70°, 80°, 80°, 80° and 80° C., and the temperature of the die was 90° C.

EXAMPLE 10

50 parts of a commercial polyvinyl acetate having a degree of hydrolysis of 80% and 50 parts of theophyllin were processed by a method similar to that described in Example 1. The temperatures of the five shots were 100°, 100°, 110°, 120° and 130° C., and the temperature of the die was 150° C.

EXAMPLE 11

50 parts of polyhydroxyethyl methacrylate having a K value of 30 to 50 parts of theophyllin were processed by a method similar to that described in Example 1. The temperatures of the shots were 120°, 130°, 150°, 160° and 160° C., and the temperature of the die was 170° C.

EXAMPLES 12 TO 14

36 parts of a copolymer obtained from 60% by weight of N-vinylpyrrolidone and 40% by weight of vinyl acetate and having a K value of 30, 4 parts of stearyl alcohol, 40 parts of theophyllin and 20 parts of starch (Example 12), lactose (Example 13) or sucrose (Example 14) were mixed in a 6-shot twin-screw extruder and shaped into tablets by a method similar to that described in Example 1. The temperatures of the shots were 90°, 100°, 110°, 120°, 120° and 130° C., and the temperature of the die was 135° C.

EXAMPLES 15 TO 17

50 parts of the copolymer of Examples 12 to 14 and 50 parts of verapamil were shaped into tablets as described in Examples 12 to 14.

The following Examples were carried out similarly to the above Examples. The processing conditions and the release rates in the half-change test (cf. R. Voigt, Lehrbuch der pharmazeutischen Technologie, 5th edition, Verl. Chemie, Weinheim; Deerfield Beach, Fla.; Basle, 1984, page 627, in conjunction with the paddle method according to USP 21) are shown in the Table.

TABLE

| Example No. | Active compound | Polymer | Auxiliary | Weight ratio active compound/ polymer/auxiliary | T1 | T2 | T3 | T4 | T5 | T6 | Die | Release rate |
|---|---|---|---|---|---|---|---|---|---|---|---|---|
| 18 | Pseudoephedrine 47.5 Diphenhydramine 2.5 | A | ./. | 50/50/0 | 60 | 80 | 100 | 120 | 120 | 120 | 120 | 100% in 1 h |
| 19 | Propafenone | A | starch | 40/40/20 | 60 | 70 | 90 | 110 | 110 | 110 | 110 | 100% in 1 h |
| 20 | Propafenone | A | StA | 60/35/5 | 80 | 90 | 100 | 120 | 140 | 140 | 140 | 100% in 2 h |
| 21 | Propafenone | A | StA | 60/30/10 | 80 | 90 | 100 | 120 | 130 | 130 | 140 | 52% in 6 h |
| 22 | Propafenone | A | StS | 60/35/5 | 70 | 90 | 100 | 110 | 115 | 115 | 115 | 42% in 6 h |
| 23 | Propafenone | B | StA | 50/40/10 | 65 | 80 | 95 | 110 | 110 | 110 | 110 | 100% in 6 h |
| 24 | Propafenone | A | MgSt | 60/35/5 | 60 | 70 | 80 | 80 | 95 | 100 | 100 | 95% in 6 h |
| 25 | Propafenone | A | MgSt | 50/40/10 | 60 | 70 | 80 | 80 | 95 | 100 | 100 | 80% in 6 h |
| 26 | Anipamil | A | MgSt | 50/40/10 | 30 | 30 | 40 | 40 | 60 | 60 | 60 | 100% in 2 h |
| 27 | Vitamin B1 | B | ./. | 50/50/0 | 40 | 40 | 50 | 60 | 80 | 80 | 80 | 100% in 1 h |
| 28 | Nicotinic acid | A | ./. | 50/50/0 | 60 | 70 | 80 | 95 | 95 | 100 | 100 | 100% in 1 h |
| 29 | Biperiden | A | StA | 50/45/5 | 80 | 90 | 100 | 120 | 120 | 130 | 135 | 100% in 4 h |
| 30 | Biperiden | A | ./. | 50/50/0 | 80 | 90 | 110 | 120 | 140 | 140 | 140 | 100% in 1 h |
| 31 | Canthaxanthin | B | ./. | 50/50/0 | 30 | 30 | 40 | 40 | 60 | 60 | 60 | 100% in 1 h |
| 32 | Canthaxanthin | A | ./. | 50/50/0 | 40 | 40 | 55 | 60 | 60 | 80 | 80 | 100% in 1 h |

| Example No. | Active compound | Polymer | Weight ratio active compound/polymer | T1 | T2 | T3 | T4 | T5 | T6 | Die |
|---|---|---|---|---|---|---|---|---|---|---|
| 33 | Indomethacin | A | 25/75 | 50 | 60 | 70 | 80 | 80 | 80 | 80 |
| 34 | Indomethacin | B | 25/75 | 60 | 80 | 100 | 120 | 120 | 120 | 120 |
| 35 | Anipamil | A | 25/75 | 30 | 30 | 40 | 50 | 50 | 60 | 60 |
| 36 | Anipamil | B | 25/75 | 30 | 30 | 40 | 50 | 50 | 60 | 60 |
| 37 | Benzocaine | D | 25/75 | 60 | 80 | 95 | 100 | 120 | 120 | 140 |

TABLE-continued

| | | | | | | | | | | |
|---|---|---|---|---|---|---|---|---|---|---|
| 38 | Benzocaine | D | 25/75 | 60 | 80 | 95 | 100 | 120 | 130 | 140 |
| 39 | Benzocaine | F | 25/75 | 30 | 30 | 40 | 50 | 50 | 60 | 60 |
| 40 | Benzocaine | B | 25/75 | 60 | 80 | 100 | 120 | 120 | 120 | 120 |
| 41 | 5,5-Diphenhydramine | B | 25/75 | 60 | 80 | 100 | 120 | 120 | 120 | 120 |
| 42 | Paracetamide | B | 25/75 | 60 | 80 | 100 | 120 | 120 | 120 | 120 |
| 43 | Sulfathiazole | B | 25/75 | 70 | 90 | 100 | 100 | 100 | 100 | 120 |
| 44 | Sulfathiazole | E | 25/75 | 70 | 90 | 100 | 100 | 100 | 110 | 120 |
| 45 | Benzocaine | A | 25/75 | 30 | 30 | 40 | 50 | 60 | 70 | 70 |
| 46 | 5,5-Diphenhydramine | A | 25/75 | 60 | 80 | 100 | 120 | 120 | 120 | 130 |
| 47 | Paracetamol | A | 25/75 | 60 | 80 | 100 | 120 | 120 | 120 | 130 |
| 48 | Sulfathiazole | A | 50/50 | 70 | 90 | 100 | 100 | 100 | 100 | 130 |
| 49 | Vitamin C | C | 50/50 | 75 | 95 | 95 | 120 | 120 | 120 | 120 |
| 50 | Benzocaine | E | 25/75 | 60 | 70 | 80 | 120 | 130 | 130 | 130 |
| 51 | Benzocaine | G | 25/75 | 60 | 70 | 70 | 80 | 80 | 80 | 120 |
| 52 | Benzocaine | H | 25/75 | 50 | 60 | 60 | 60 | 80 | 90 | 110 |
| 53 | Benzocaine | I | 25/75 | 50 | 60 | 70 | 70 | 75 | 75 | 80 |

A = Copolymer of 60% by weight of NVP and 40% by weight of vinyl acetate, K value about 33
B = PVP, K value 12
C = PVP, K value 17
D = Mowiol ® 30-92 (92% hydrolyzed polyvinyl alcohol)
E = Mowiol 4-80 (80% hydrolyzed polyvinyl alcohol)
F = Copolymer of NVP, vinyl acetate and hydroxypropyl acrylate in a weight ratio of 30/40/30; K value about 18
G = Cellulose acetate
H = Cellulose acetate phthalate
I = Vinyl acetate/crotonic acid copolymer; K value about 30
StA = Stearyl alcohol
StS = Stearic acid
MgSt = Magnesium stearate

We claim:
1. A continuous method for producing separate tablets of an extrudable pharmaceutical mixture which comprises:

mixing a pharmaceutically active compound and an N-vinylpyrrolid-2-one (NVP) polymer containing 30 to 100% by weight NVP in an extruder to form a melt, said polymer having a K value of from 10 to 100, said mixture having a glass transition point of less than 180° C.;

extruding the melt and pressing the still deformable extrudate between the surfaces of two rollers driven in opposite directions, the surfaces of said rollers having opposed depressions, whereby, separate tablets having the shape of the opposed depressions are formed.

2. The method of claim 1, wherein an active compound-containing melt of an N-vinylpyrrolid-2-one (NVP) polymer is extruded and pressed, the NVP polymer being prepared either in an organic solvent or using an organic peroxide in water.

3. The method of claim 1, wherein the K value of the polymer is from 12 to 35 and the mixture has a softening or melting point of from 60° to 130° C. and a glass transition point of less then 130° C.

* * * * *